United States Patent [19]  [11] 4,186,270
Dowd et al.  [45] Jan. 29, 1980

[54] PROCESS FOR MAKING 2-(4-ISOBUTYLPHENYL)PROPIONIC ACID AND RELATED COMPOUNDS

[75] Inventors: William Dowd; David H. Naffziger, both of Midland, Mich.

[73] Assignee: The Dow Chemical Company, Midland, Mich.

[21] Appl. No.: 973,206

[22] Filed: Dec. 26, 1978

[51] Int. Cl.$^2$ .................. C07C 63/33; C07C 63/52
[52] U.S. Cl. .................. 562/496; 260/465 R; 260/651 HA; 562/492
[58] Field of Search .................. 260/465 R; 562/492, 562/496

[56] References Cited

U.S. PATENT DOCUMENTS

| | | | |
|---|---|---|---|
| 3,228,831 | 1/1966 | Nicholson et al. | 562/496 X |
| 3,385,886 | 5/1968 | Nicholson et al. | 562/492 |
| 4,031,243 | 6/1977 | Aparicio et al. | 562/496 X |
| 4,056,509 | 11/1977 | Verbrugge et al. | 260/465 R |

*Primary Examiner*—Dolph H. Torrence

[57] ABSTRACT

Pure 2-(4-isobutylphenyl)propionic acid and related compounds are obtained in good yield by a multi-step process comprising chloromethylation of benzene or an alkylbenzene, conversion of the resulting benzyl chloride to the cyanide, alkylation of that product to the phenylpropionitrile or phenylbutyronitrile, reaction of unreacted benzyl cyanide with an aldehyde to inhibit its hydrolysis, and hydrolysis of the nitrile to the free acid. The products are antiinflammatory, antipyretic, and analgesic drugs.

11 Claims, No Drawings

PROCESS FOR MAKING 2-(4-ISOBUTYLPHENYL)PROPIONIC ACID AND RELATED COMPOUNDS

BACKGROUND OF THE INVENTION

This invention relates to a new chemical process, more particularly to a multistep process whereby a good yield of a pure compound is produced at the final step without the need for separation or purification of intermediate reaction products. The invention relates particularly to the use of a supplementary reaction to eliminate a toxic impurity.

Substituted propionic and butyric acids having the structure

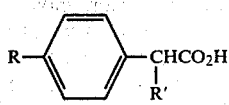

wherein R is hydrogen, an alkyl group of 1-7 carbon atoms, or a cycloalkyl group of 5-7 carbon atoms and R' is methyl or ethyl and esters and salts thereof are relatively recently discovered drugs useful for treating inflammation, pain, and fever in man and other animals. Preferred compounds are those where R is a branched alkyl group of 3-7 carbon atoms or a cycloalkyl group. A particularly useful member of this class is 2-(4-isobutylphenyl)propionic acid, also known as ibuprofen, an antiinflammatory drug used for the symptomatic treatment of arthritis and other rheumatic conditions. As compared to earlier known drugs used for the same purpose, for example, aspirin, corticosteroids, and phenylbutazone, ibuprofen has one or more of the advantages of being less irritating and less prone to cause ulcers in the digestive tract on prolonged use, lower toxicity, higher therapeutic ratio, higher solubility in water, and better stability in the presence of moisture. Another member of this class of compounds with similar useful properties is the corresponding butyric acid known as butibufen.

Many processes for the synthesis of these compounds have been described in the art, none of which is completely satisfactory. Because of their molecular structure, no simple procedure for the synthesis is possible. The synthetic routes described in the literature not only include many separate chemical operations, but also often require expensive or unusual reagents. In addition, these known procedures may involve low yields or undesirably high production of wastes which must be disposed of. Because of the toxicity of certain isomers, homologs, or other possible by-products of a synthesis, some synthetic routes may appear to be impractical because they involve excessive separation and purification procedures for intermediates or for the final product. Representative references describing processes for making ibuprofen and related compounds or intermediates therefor include U.S. Pat. Nos. 3,228,831; 3,385,886; and 3,933,864 and Swiss Pat. Nos. 573,386 and 573,891. The first two U.S. patents in particular (see column 3, lines 40-45 of U.S. Pat. No. 3,228,831) schematically describe a process wherein an alkylbenzene is chloromethylated to make the corresponding alkylbenzyl chloride, the alkylbenzyl chloride is reacted with a cyanide to make the alkylphenylacetonitrile, and the alkylphenylacetonitrile is methylated to produce the 2-(alkylphenyl)propionitrile which is then converted to the carboxylic acid by hydrolysis. However, conventional reaction and separation procedures in such a multistep process where a number of difficulty separable isomers, homologs, and other reaction by-products are inevitably formed would appear to limit that process to low yields and require extensive purification in order to make a final product of the requisite high quality.

SUMMARY OF THE INVENTION

It has now been found that compounds of the above structure in general and ibuprofen in particular are produced in good yield and high purity by a series of reactions using common and readily available reagents and involving minimal processing of the various reaction mixtures with no separation or purification of the intermediate organic products. This process comprises (a) reacting a compound of the formula

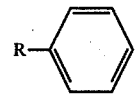

with a chloromethyl ether or chloromethyl ester in the presence of a solvent under chloromethylating conditions to produce a solvent solution of the corresponding benzyl chloride

(b) reacting that solution with at least about one molar equivalent of metal cyanide in aqueous solution per mole of the benzyl chloride at about 60° C. 100° C. in the presence of a solubilizing amount of a phase-transfer catalyst, thereby producing an organic layer consisting essentially of a phenylacetonitrile of the formula

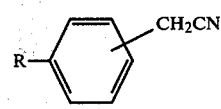

and reaction solvent and an aqueous layer containing dissolved inorganic salts, separating the organic layer and distilling from it essentially all of the solvent to form a distillation residue of the crude phenylacetonitrile, (c) reacting said crude phenylacetonitrile with about 0.8-1.5 molar equivalents of alkyl halide or dialkyl sulfate wherein alkyl is methyl or ethyl in the presence of excess alkali metal hydroxide at about 0° C.-70° C., thereby producing a reaction mixture consisting essentially of the monoalkylated nitrile of the formula

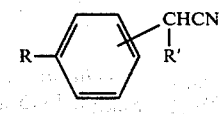

wherein R' is methyl or ethyl and minor proportions of the unreacted phenylacetonitrile and the dialkylated by-product, (d) reacting that reaction mixture at about 20° C.–60° C. with at least about one mole per mole of the unreacted phenylacetonitrile of an aldehyde of the formula R"CHO wherein R" is a hydrocarbon radical of 2–10 carbon atoms or a furyl radical, washing the reacted mixture with water, (e) reacting the washed mixture at about 100° C.–120° C. for 1–15 hours with at least about one mole of about 60–80 percent aqueous $H_2SO_4$ per mole of total nitrile content in the presence of sufficient acetic acid to make a homogeneous solution, and separating a compound of the formula

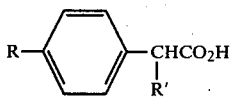

from the thereby formed hydrolysis product.

The invention also comprises the use of the aldehyde reaction of step (d) above as a specific improvement in the broadly described sequence of process reactions.

In the above-described sequence of process steps, with the exception of solvent removal at the end of step (b), only water-soluble impurities and by-products are separated from the various reaction mixtures during the process. Surprisingly, although a number of isomers, homologs, and other organic by-products are produced in the various process steps and remain in the reaction mixture, relatively pure product is readily separable in good yield from the mixture at the end of the process, ordinarily by crystallization, and only minimal purification of that separated product, usually by a single recrystallization, is required to obtain material of pharmaceutically acceptable quality. When R represents an alkyl or cycloalkyl substituent, the separated product is the desired para substituted acid.

DETAILED DESCRIPTION OF THE INVENTION

The chloromethylation step is accomplished under conventional chloromethylation conditions, i.e., by reacting benzene or a substituted benzene with a chloromethyl ether at a moderate temperature of about 20° C.–75° C., preferably at about 40° C.–65° C., using an acid or acidic metal salt catalyst and preferably in the presence of a solvent. Catalysts for the reaction include strong acids such as HCl, $H_2SO_4$, and chlorosulfonic acid as well as acidic metal salts such as chlorides, sulfates or acetates of iron, zinc, titanium, aluminum, or antimony and also compounds which are converted to such salts under the conditions of the chloromethylation reactions, for example, hydroxides or oxides of these metals. In the present process, superior results have been obtained by using a zinc compound such as zinc oxide or zinc hydroxide in a quantity of about 0.05–0.25 atom of zinc per mole of the benzene reactant, a small excess of the latter preferably serving as a reaction diluent and solvent. Other organic solvents which are inert under reaction conditions such as ethylene dichloride, methylene chloride, dichlorobenzene, and the like can be used as reaction solvents but these may complicate the product workup and separation procedures. A reaction time of about 1–15 hours, depending upon the reaction temperature, is ordinarily sufficient for this step.

The chloromethylating reagent is preferably chloromethyl methyl ether, bis(chloromethyl) ether, or a mixture thereof. The less toxic chloromethyl methyl ether is preferred and this is conveniently prepared in situ using a mixture of dry HCl, formaldehyde, and methanol in appropriate proportions. A ratio of about 0.5–2.5 moles of chloromethyl ether, preferably about 1.0–1.5 moles, per mole of the benzene reactant has been found to provide an optimum combination of conversion and yield of the desired benzyl chloride. Under these conditions, a benzene conversion of about 90 percent is obtained. When a substituted benzene such as isobutylbenzene is chloromethylated under these conditions, approximately 80 percent of the converted material is converted to the para isomer, most of the remainder appearing in the reaction mixture as the ortho isomer and as methylenebis(isobutylbenzene).

Similar results are obtained using other chloromethyl ethers under the same conditions. Such ethers include chloromethyl propyl ether, chloromethyl isobutyl ether, chloromethyl isoamyl ether, and the chloromethyl ether of a polyethylene glycol monoether. Chloromethyl esters of lower alkanoic acids such as chloromethyl acetate and chloromethyl propionate are also known chloromethylating reagents and these too serve in the present process.

The chloromethylation reaction product consists of two liquid phases, an aqueous phase containing the catalyst and excess HCl and an organic phase which may also contain some HCl, traces of water and possibly some unreacted chloromethyl ether. The organic layer is preferably washed to remove HCl and stripped of small amounts of lights under reduced pressure before passing to the cyanide reaction step of the process. Optimum results are obtained using excess benzene or substituted benzene reactant as the reaction solvent and vacuum stripping the organic layer from the chloromethylation reaction to obtain a solution consisting essentially of about 40–60 percent by weight of benzyl chloride product in the starting aromatic hydrocarbon reactant.

The solution of the benzyl chloride product is reacted with an aqueous solution of a metal cyanide by intimately contacting the two solutions to form the corresonding organic cyanide, a phenylacetonitrile. Preferably, this reaction is carried out at about 70° C.–90° C. using the metal cyanide in moderate excess, for example, about 1.2–1.5 moles per mole of chloride. Any water-soluble metal cyanide can be used such as calcium cyanide or other alkaline earth metal cyanide but an alkali metal cyanide, usually sodium cyanide, is ordinarily most practical. Ammonium cyanide is also included in this latter group. The best separation of organic and aqueous layers at the end of the reaction is obtained by using sodium cyanide in 20–40 percent aqueous solution. The reaction is rapid and is essentially complete in a few minutes. To accomplish these results, it is necessary to incorporate in the reaction mixture a small amount of a phase-transfer catalyst. Phase-transfer catalysts and their applications are described by Napier and Starks, U.S. Pat. No. 3,992,432, see also Phase Transfer Catalysis in Organic Synthesis, Weber and Gokel, Springer-Verlag, Berlin (1977). These compounds include the quaternary salts of Group VB elements of the periodic table, particularly ammonium and phosphonium chlorides, bromides, and bisulfates such as methyltributylammonium chloride, benzyltriethylammonium bromide, methyltrioctylammonium chloride, tetrabutylammonium bisulfate, and corresonding phosphonium salts. The most effective compounds are those where the hydrocarbon substituents contain a total of about 18–40 carbon atoms. Other known phase-transfer catalysts effective in this process are the crown ethers, cyclic oligomers of ethylene oxide such as 18-crown-6 and dicyclohexyl-18-crown-6. Quaternary ammonium salts are preferred. Any quantity of phase-transfer catalyst sufficient to solubilize the aqueous cyanide in the organic phase to a significant degree is operable. A quantity of about 0.005–0.1 mole of phase-transfer catalyst per mole of benzyl chloride reactant can be used effectively. Preferably, a mole ratio of about 0.01–0.05:1 is employed.

The resulting two-phase reaction mixture is preferably cooled and diluted with water before the organic layer, consisting essentially of a solution of the phenylacetonitrile in the reaction solvent plus organic by-products, is separated and essentially all of the reaction solvent, preferably excess bezene reactant, is distilled off to obtain the crude nitrile as the distillation residue. The distilled solvent is recycled to the process and the aqueous salt layer is discarded.

In the third step of the process, the crude nitrile is reacted with about an equivalent amount of an alkylating agent, preferably a methyl or ethyl halide or dimethyl or diethyl sulfate. A methyl or ethyl halide such as chloride, bromide, or fluoride is preferred and methyl or ethyl chloride is most preferred for their lower price price and good reactivity. The alkylation reaction is carried out in the presence of excess strong alkali as acid receptor, preferably aqueous NaOH of about 40–50 percent concentration. The reaction is preferably carried out at about 0° C.–50° C., most preferably at about 30° C.–50° C. using about 0.9–1.05 mole of alkyl chloride per mole of nitrile, and about 2–4 moles of alkali metal hydroxide. The phase-transfer catalyst from the cyanide reaction described above largely remains in the crude nitrile from the second step of the process and also facilitates this reaction. The reaction is essentially completed in about 0.1–10 hours under the conditions outlined above to produce a mixture in which about 70 percent of the nitrile has been monoalkylated to the corresponding propionitrile or butyronitrile, 15–20 percent has been dialkylated, and about 10–15 percent remains unreacted. Of all of the organic reaction by-products to this point, including the unreacted nitrile, the dialkylated nitrile, and other minor by-products originating earlier in the process, the unreacted nitrile is most undesirable, because it and its toxic hydrolysis product are not readily separable from the mixture by practical physical means. Therefore, this unreacted nitrile is converted by chemical means to another compound which does not interfere with the ultimate separation of a pure product.

This chemical modification of the unwanted component is accomplished by reacting it with at least about one mole and preferably a slight excess of an aldehyde of 3–8 carbon atoms such as propionaldehyde, butyraldehyde, hexanal, octanal, furaldehyde, benzaldehyde, or tolualdehyde in the same temperature range used for the alkylation reaction. The reaction is very rapidly complete so that the undesirable starting material is essentially comletely removed from the reaction mixture by the reaction with elimination of the elements of water of the aldehyde group with the two hydrogen atoms alpha to the cyanide group of the phenylacetonitrile. The resulting condensation product remains in the reaction mixture but does not interfere in the final separation of the desired pure product from that and the isomers, homologs, and other organic by-products in that mixture. The desired monoalkylated nitrile and the dialkylated by-product both lack the two hydrogen atoms alpha to the cyanide group and thus they cannot react with an aldehyde in the same way. Aldehydes other than those defined above also react in the same way but the reaction products interfere with product separation and purification.

After the aldehyde reaction, the reaction mixture is diluted with water and the resulting organic product layer is separated from the aqueous caustic brine. The layer separation is facilitated by using enough water to produce a brine layer containing about 5 percent dissolved solids. The organic layer is essentially free of inorganic compounds.

The washed organic layer is then reacted with an acid solution consisting of about 60–80 percent aqueous $H_2SO_4$ and acetic acid sufficient to make a homogeneous solution. The sulfuric acid is present in a quantity of at least about one mole per mole of nitrile, preferably about 1–1.5 moles with three or more moles of water. Sulfuric acid of 65–75 percent concentration is preferred. Under these preferred conditions, about four moles of acetic acid is sufficient to make a homogeneous solution of all components. This acid mixture is heated, preferably at its reflux temperature, for about 5–10 hours to obtain substantially complete hydrolysis of the desired phenylpropionitrile or phenylbutyronitrile to the corresponding carboxylic acid.

The desired product can be separated from the hydrolyzed mixture by conventional means. Preferably, the acetic acid is first stripped from the mixture by distillation at reduced pressure. This procedure also removes remaining excess benzene or substituted benzene which comes over as an azeotrope with acetic acid and can be recovered for recycle by diluting the distillate with water. The organic distillation residue can be washed with a mixture of water and a hydrocarbon solvent such as octane or benzene to separate water-soluble impurities, the organic solvent layer then extracted with aqueous NaOH to separate the organic acid components from neutral organic impurities, the basic extract acidified in the presence of octane or other such solvent to liberate the acid product, and then recovered from the octane solution by crystallization. Further purification of the acid product to the desired degree of purity is readily accomplished by recrystallization and treatment with a decolorizing agent such as activated carbon. Additional product can be recovered by conventional treatment of the mother liquors.

Surprisingly, a good yield of a pharmaceutically acceptable grade of product is obtained by the above-outlined procedure even though various isomeric, homologous, or other related organic by-products remain in the crude product throughout this multistep process with no intermediate purification or organic by-product separation. Except for solvent distillation, only water-soluble impurities and by-products are removed at each step utilizing simple liquid layer separations.

Example 1–4 describe in detail a preferred mode of operating the process using isobutylbenzene as the starting benzene reactant to make the antiarthritic drug ibuprofen (2-(4-isobutylphenyl)propionic acid).

EXAMPLE 1

To 621 g of 55 percent aqueous formaldehyde (11.4 g moles of HCHO) was added 212 g of methanol and 402 g of isobutylbenzene. The mixture was cooled to about 10° C. and 490 g of HCl gas was sparged in over a period of 1.5 hours while the temperature was maintained below 35° C. After the HCl addition, agitation was stopped and the upper layer was separated. This was found to contain 8.5 g moles of chloromethyl methyl ether.

The chloromethyl methyl ether solution was combined with a slurry of 98 g of ZnO in 415 g of isobutylbenzene at 10° C. After the cooling bath was removed, the temperature of the reaction mixture rose to about 50° C. The mixture was then heated and stirred at 60° C. for two hours, cooled to about 35° C., and the upper, organic layer was separated. This was washed with successive 500 g portions of water, 20 percent aqueous NaOH, and water. The final washed product weighed 1156 g and consisted essentially of a solution of isobutylbenzyl chloride isomers in excess isobutylbenzene with some lights (methanol, methylal, and a little water) and a small amount of highers, chiefly methylenebis(isobutylbenzene). The isomeric distribution in the isobutylbenzyl chloride product was 87.5 percent para, 12.0 percent ortho, and 0.5 percent meta. The p-isobutylbenzyl chloride present amounted to 730 g or 4.0 g moles, an 82.2 percent yield based on the isobutylbenzene reacted.

EXAMPLE 2

A portion of crude isobutylbenzyl chloride solution prepared as in Example 1 was combined with 50 percent excess NaCN based on the chloride present, water to make a 40 percent cyanide solution, and 1 percent of a phase-transfer catalyst based on the weight of isobutylbenzyl chloride. The catalyst used was a methyltrialkylammonium chloride where alkyl=$C_{8-10}$. The reaction mixture was stirred and heated at 80° C. for 4.5 hours, at which time the reaction was essentially completed. The mixture was cooled to about 40° C. and the upper, organic layer was separated and distilled at 25 mm Hg to a pot temperature of 125° C. to remove lights and most of the isobutylbenzene. The crude isobutylbenzyl cyanide or (isobutylphenyl)acetonitrile product represented a yield of better than 95 percent of the theoretical amount based on the starting chloride.

EXAMPLE 3

Crude (isobutylphenyl)acetonitrile from the process of Example 2 was combined with three times the molar equivalent amount of 50 percent aqueous NaOH. Most of the quaternary ammonium chloride used as phase-transfer catalyst in Example 2 remained in the reaction mixture. This mixture was stirred and heated to 35° C., at which temperature methyl chloride was bubbled into the mixture until 0.95 mole per mole of nitrile had been added. After an additional 30 minutes of stirring at the reaction temperature to complete the methylation reaction, the mixture was analyzed by gas-liquid chromatography and a quantity of benzaldehyde 10 percent in excess of that theoretically required to react with the residual unreacted (4-isobutylphenyl)acetonitrile was added. The reaction mixture was stirred for 10 minutes and sufficient water was added to make an aqueous layer containing about 5 percent by weight of sodium chloride and sodium hydroxide. The organic layer consisted essentially of 2-(4-isobutylphenyl)propionitrile, isomers thereof, some dimethylated product, and the benzaldehyde-(isobutylphenyl)acetonitrile reaction product.

EXAMPLE 4

One hundred parts by weight of crude product from the process of Example 3 containing 4 molar proportions of 2-(4-isobutylphenyl)propionitrile was combined with 16 moles of acetic acid, 12 moles of water, and 6 moles of concentrated $H_2SO_4$ and the mixture was heated to reflux, taking off a smalll forecut of lights to reach the reflux temperature of acetic acid. After 8 hours at reflux, acetic acid and some residual isobutylbenzene were distilled from the mixture at progressively reduced pressure until a pot temperature of 125° C. was reached at 15 mm Hg.

The residual mixture was then cooled to 90° C. and 50 parts by weight of water plus 20 parts of octane were added and the mixture was stirred until equilibrium was reached. The octane layer was separated at 50° C.-60° C. and it was extracted twice with 5 percent aqueous NaOH in quantities in excess of that required to form the sodium salt of the product 2-(4-isobutylphenyl)propionic acid in the octane solution. The combined basic extracts were washed twice with octane to remove any entrained neutral impurities and then were acidified to pH 1 with concentrated HCl in the presence of enough octane at 50° C.-60° C. to dissolve the thereby liberated acid. This octane layer was separated at 50° C.-60° C. and enough octane was distilled off to dry it and to produce a solution containing 2 parts by weight of octane per part of dissolved solids. This solution was cooled to −10° C. to cause crystallization and the crystallized product was collected, washed with a little cold octane, then redissolved in hot octane, treated with decolorizing charcoal, and recrystallized as before to obtain white crystals assaying better than 99.5 percent 2-(4-isobutylphenyl)propionic acid and containing no detectable isobutylphenylacetic acid. Additional product was obtained from the mother liquors.

The yield of purified product based on the starting 2-(4-isobutylphenyl)propionitrile in the crude product of Example 3 was 44 percent. This was raised to about 50 percent by reworking the mother liquors.

The overall yield of the purified acid based on the isobutylbenzene reaction in the chloromethylation step of Example 1 including product recovered from mother liquors was about 42 percent.

Examples 5–9 illustrate the effects of various chloromethylation catalysts in that reaction. In each of these reactions, chloromethyl methyl ether was the chloromethylating reagent and it was prepared and used as described in Example 1 with a molar ratio of 1.2 moles of chloromethyl methyl ether per mole of isobutylbenzene as the benzene reactant. Other reaction conditions were a temperature of 40° C. and a reaction time of 2 hours. Catalyst ratios were 0.1 mole per mole of isobutylbenzene except for sulfuric acid in which case 0.5 mole of acid was used. Results are listed in Table I.

TABLE I

| Example No. | Catalyst | % Conversion isobutylbenzene | % Selectivity* p-isomer | methylenebis by-product |
|---|---|---|---|---|
| 5 | $SnCl_4$ | 19 | 56 | 36 |

TABLE I-continued

| Example No. | Catalyst | % Conversion isobutyl- benzene | % Selectivity* p-isomer | methyl- enebis by-product |
|---|---|---|---|---|
| 6 | Ferric acetate | 44 | 45 | 47 |
| 7 | H₂SO₄ | 41 | 57 | 34 |
| 8 | ZnO | 46 | 78 | 10 |
| 9 | Zn(OH)₂ | 22 | 82 | 6 |

*percent of converted isobutylbenzene appearing as that compound

The ratio of p-isomer to o-isomer in the product was essentially constant at 87:13 in these reactions.

Examples 10-12 show the effects of varying the temperature in the chloromethylation reaction. These reactions were run using ZnO catalyst at 0.2 mole per mole of isobutylbenzene and a reaction time of three hours with other conditions as in Example 8.

TABLE II

| Example No. | Temp. °C. | % Conversion isobutylbenzene | % Selectivity to p-isomer |
|---|---|---|---|
| 10 | 40 | 48 | 76 |
| 11 | 50 | 66 | 73 |
| 12 | 60 | 84 | 66 |

Results comparable to those shown in Examples 5-12 are obtained when those procedures are repeated using benzene, another alkylbenzene, or a cycloalkylbenzene in place of isobutylbenzene.

Experiments run essentially as described in Examples 1 and 12 using chloromethyl methyl ether, chloromethyl propyl ether, chloromethyl isobutyl ether, and chloromethyl isoamyl ether respectively as the chloromethylating reagent showed a slightly improved ratio of para to ortho isomer in the product but the improvement due to the larger alkyl group in the reagent was insufficient to overcome the practical disadvantages of these other chloromethylating reagents.

Examples 13-15 represent essentially variations of Example 3 wherein methyl chloride was reacted with p-isobutylphenylacetonitrile at different temperatures and different molar ratios of reactants. Other reaction conditions are as described in Example 3. Molar percentages of dimethylated nitrile, the desired monomethylated nitrile, and unreacted nitrile are listed in the tables for each mole ratio of CH₃Cl to nitrile.

EXAMPLE 13

| Reactant Ratio | Temperature = 10° C. | | | | | |
|---|---|---|---|---|---|---|
| | 1.0 | 1.1 | 1.2 | 1.3 | 1.5 | 1.7 |
| di | 15 | 16 | 20 | 22 | 29 | 29 |
| mono | 62 | 69 | 71 | 70 | 67 | 68 |
| unreacted | 23 | 15 | 9 | 8 | 4 | 3 |

EXAMPLE 14

| Reactant Ratio | Temperature = 45° C. | | | | | |
|---|---|---|---|---|---|---|
| | 0.5 | 0.8 | 1.0 | 1.1 | 1.2 | 1.4 |
| di | 4 | 7 | 15 | 18 | 22 | 30 |
| mono | 48 | 61 | 70 | 71 | 71 | 66 |
| unreacted | 48 | 32 | 15 | 11 | 7 | 4 |

EXAMPLE 15

| Reactant Ratio | Temperature = 65° C. | | | | | |
|---|---|---|---|---|---|---|
| | 0.5 | 0.8 | 1.0 | 1.1 | 1.2 | 1.4 |
| di | 7 | 13 | 21 | 28 | 38 | 51 |
| mono | 59 | 69 | 70 | 66 | 60 | 48 |
| unreacted | 84 | 18 | 9 | 6 | 2 | 1 |

The reactions of Examples 16 and 17 were run in the same way as those of Examples 13-15 using other methylating reagents. In Example 17, 10 mole percent of phase-transfer catalyst was used instead of the usual 2 percent to speed up the reaction rate.

EXAMPLE 16

| Reactant Ratio | Temperature = 50° C. Methylating reagent - dimethyl sulfate | | | | |
|---|---|---|---|---|---|
| | 0.5 | 0.75 | 1.0 | 1.25 | 1.5 |
| di | 1 | 6 | 5 | 13 | 13 |
| mono | 26 | 29 | 30 | 38 | 44 |
| unreacted | 73 | 65 | 65 | 49 | 43 |

EXAMPLE 17

| Reactant Ratio | Temperature = 50° C. Methylating reagent - methyl bromide | | | | | |
|---|---|---|---|---|---|---|
| | 0.5 | 0.8 | 1.0 | 1.1 | 1.2 | 1.4 |
| di | 3 | 7 | 9 | 13 | 17 | 18 |
| mono | 47 | 61 | 62 | 69 | 69 | 70 |
| unreacted | 50 | 32 | 29 | 18 | 14 | 12 |

Similar effects from varying the temperature, reactant ratio, or alkylating agent are obtained when the alkylating agent in the procedures of Examples 13-17 is ethyl chloride, ethyl bromide, or diethyl sulfate. Additionally, methyl fluoride or ethyl fluoride can be used as the alkylating reagent under the above-defined conditions to obtain results similar to those found with the corresponding chlorides.

The reaction of benzaldehyde or other such aldehyde with residual phenylacetonitrile or alkylphenylacetonitrile remaining in the methylation reaction product (see Example 3) is a critical step necessary for the separation of a pure product in the final step of this process. Examples 18-21 illustrate the effect obtained by adding various amounts of benzaldehyde to distilled methylation reaction product as obtained in Example 3 wherein the mole ratio of 2-(isobutylphenyl)propionitrile (mono) to the dimethylated by-product (di) was 3.86/1 and the mole ratio of unreacted isobutylphenylacetonitrile (BPA) to dimethylated by-product was 0.86/1. These reactions were carried out at the normal methylation reaction temperature of 35° C. for 15 minutes. The resulting reaction mixtures were analyzed chromatographically as before.

TABLE III

| Example No. | Moles Aldehyde per mole BPA | Mole Ratios mono/di | BPA/di |
|---|---|---|---|
| blank | 0 | 3.86 | 0.86 |
| 18 | 0.5 | 3.80 | 0.35 |

TABLE III-continued

| Example No. | Moles Aldehyde per mole BPA | Mole Ratios mono/di | BPA/di |
|---|---|---|---|
| 19 | 0.75 | 3.78 | 0.15 |
| 20 | 1.00 | 3.77 | 0.06 |
| 21 | 1.25 | 3.76 | 0.00 |

When formaldehyde was substituted for benzaldehyde in the above reaction, the formaldehyde reaction product was a tar which could not be separated from the final product of the process by any practical means. When excess acetophenone was substituted for the benzaldehyde, only 30 percent of the unreacted BPA was found to have reacted with it after 6 hours under the reaction conditions. However, aldehydes such as propionaldehyde, butyraldehyde, hexanal, octanal, furfural, and tolualdehyde provide effective removal of the unreacted phenylacetonitrile after the alkylation step similar to that obtained with benzaldehyde.

The above examples are directed specifically to the production of ibuprofen, 2-(4-isobutylphenyl)propionic acid. However, the procedures and limits described in those examples are also illustrative of the application of the process to the production of other related acids of the class previously defined. Thus, by substituting cyclohexylbenzene for the isobutylbenzene starting material in Example 1 and proceeding as described in Examples 1–4, the product of the process is 2-(4-cyclohexylphenyl)propionic acid which is obtained in similar purity and yield. In the same way, when ethyl chloride is used in place of methyl chloride in the alkylation step of Example 3 and the procedures of Examples 3 and 4 are otherwise repeated, the final product is butibufen, 2-(4-isobutylphenyl)butyric acid, also obtained in good purity and yield as described. Similarly, using benzene in place of isobutylbenzene as a starting material in this process, a good yield of pure 2-phenylpropionic acid is produced. Likewise, tert-butylbenzene as the starting benzene reactant produces 2-(4-tert-butylphenyl)propionic acid, 1,1-diethylpropylbenzene produces 2-(4-(1,1-diethylpropyl)phenyl)propionic acid, and isopropylbenzene produces 2-(4-isopropylphenyl)propionic acid. In the same way, the appropriate alkylbenzene reactant and alkylating halide produce the compounds 2-(4-cyclopentylphenyl)propionic acid, 2-(4-(1-methylcyclohexyl)phenyl)propionic acid, 2-(4-tert-butylphenyl)butyric acid, 2-(4-isopentylphenyl)butyric acid, and 2-(4-cyclohexylphenyl)butyric acid.

We claim:

1. A process for making a comound having the formula

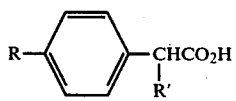

wherein R is hydrogen, an alkyl radical of 1–7 carbon atoms, or a cycloalkyl radical of 5–7 carbon atoms and R' is methyl or ethyl which comprises (a) reacting a compound of the formula

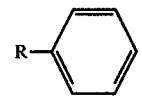

with a chloromethyl ether or ester in the presence of a solvent under chloromethylating conditions, thereby forming a solvent solution of the benzyl chloride

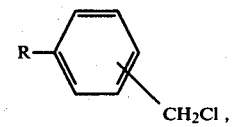

(b) reacting said solution with at least about one molar equivalent of an aqueous solution of metal cyanide per mole of the benzyl chloride at about 60° C.–100° C. in the presence of a solubilizing amount of a phase-transfer catalyst, thereby producing an organic layer consisting essentially of the corresponding phenylacetonitrile and solvent and an aqueous layer containine dissolved inorganic salts, separating said organic layer, and distilling therefrom essentially all of the solvent to form a distillation residue of the crude phehylacetonitrile

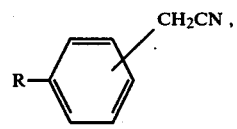

(c) reacting said crude phenylacetonitrile with about 0.8–1.5 molar equivalents of R'X or R'$_2$SO$_4$ wherein X is halogen in the presence of excess alkali metal hydroxide at about 0° C.–70° C., thereby producing a reaction mixture consisting essentially of the monoalkylated nitrile

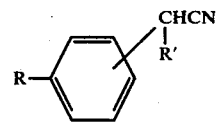

and minor proportions of the unreacted phenylacetonitrile and the dialkylated nitrile

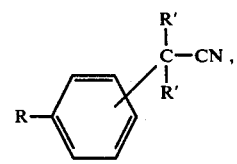

(d) reacting said reaction mixture at about 20° C.–60° C. with at least about one mole er mole of the unreacted phenylacetonitrile of an aldehyde of the formula R"CHO wherein R" is a hydrocarbon radical of 2–7 carbon atoms, water-washing the reacted mixture essentially free of inorganic salts, and (e) reacting the washed mixture at about 100° C.−120° C. for about 1–15 hours with at least about one mole of about 60–80 percent aqueous $H_2SO_4$ per mole of total nitrile in the presence of sufficient acetic acid to make a homogeneous solution, and separating $$R-\text{C}_6\text{H}_4-\underset{R'}{\text{CHCO}_2\text{H}}$$

from the thereby formed hydrolysis product.

2. The process of claim 1 wherein R' is methyl.

3. The process of claim 2 wherein R is isobutyl and the product is 2-(4-isobutylphenyl)propionic acid.

4. The process of claim 1 wherein about 0.005–0.1 mole of phase-transfer catalyst per mole of the benzyl chloride is present in step (b).

5. The process of claim 4 wherein the phase-transfer catalyst is a tetraalkylammonium salt.

6. A process for making 2-(4-isobutylphenyl)propionic acid which comprises
   (a) reacting isobutylbenzene with chloromethyl methyl ether at about 40° C.–65° C. in the presence of a zinc compound, thereby forming a solution of isobutylbenzyl chloride in isobutylbenzene,
   (b) reacting said solution with at least about one molar equivalent of an aqueous solution of an alkali metal cyanide per mole of isobutylbenzene chloride at about 60° C.–100° C. in the presence of a solubilizing amount of a phase-transfer catalyst, thereby producing an organic layer consisting essentially of (isobutylphenyl)acetonitrile and isobutylbenzene and an aqueous layer containing dissolved inorganic salts, separating said organic layer and distilling therefrom essentially all of the isobutylbenzene to form a distillation residue of crude (isobutylphenyl)acetonitrile,
   (c) reacting said crude (isobutylphenyl)acetonitrile with about 0.9–1.05 molar equivalents of methyl chloride in the presence of excess alkali metal hydroxide at about 30° C.–50° C., thereby producing a reaction mixture consisting essentially of 2-(isobutylphenyl)propionitrile and minor proportions of unreacted (isobutylphenyl)acetonitrile and 2-(isobutylphenyl)-2-methylpropionitrile,
   (d) reacting said reaction mixture at about 20° C.–60° C. with at least about one mole of benzaldehyde per mole of (isobutylphenyl)acetonitrile, water-washing the reacted mixture essentially free of inorganic salts, and
   (e) reacting the water-washed mixture at about 100° C.–120° C. for about 1–15 hours with at least about one mole of about 60–80 percent aqueous $H_2SO_4$ per mole of total nitrile in the presence of sufficient acetic acid to make a homogeneous solution, and separating 2-(4-isobutylphenyl)propionic acid from the thereby formed hydrolysis product.

7. The process of claim 1 wherein R' is ethyl.

8. The process of claim 7 wherein R is isobutyl and the product is 2-(4-isobutylphenyl)butyric acid.

9. In the process for making a compound having the formula $$R-\text{C}_6\text{H}_4-\underset{R'}{\text{CHCO}_2\text{H}}$$

wherein R is hydrogen, an alkyl radical of 1–7 carbon atoms, or a cycloalkyl radical of 5–7 carbon atoms and R' is a methyl or ethyl radical which comprises the step of reacting the phenylacetonitrile having the formula $$R-\text{C}_6\text{H}_4-\text{CH}_2\text{CN}$$

with a methylating or ethylating reagent to produce a mixture comprising the methylated or ethylated product and the unreacted phenylacetonitrile, the improvement comprising reacting said mixture at about 20° C.–60° C. with at least about one mole per mole of unreacted phenylacetonitrile of an aldehyde having the formula R"CHO wherein R" is a hydrocarbon radical of 2–7 carbon atoms or a furyl radical.

10. The process of claim 9 wherein R is isobutyl and R' is methyl.

11. The process of claim 10 wherein the aldehyde is benzaldehyde.

* * * * *